(12) United States Patent
Kim

(10) Patent No.: US 6,858,036 B1
(45) Date of Patent: Feb. 22, 2005

(54) DEVICE FOR ACUPUNCTURE

(76) Inventor: Chi-Kyung Kim, 173 Sangil-dong, Kangdong-gu, Seoul, 134-090 (KR)

( * ) Notice: Subject to any disclaimer, the term of this patent is extended or adjusted under 35 U.S.C. 154(b) by 0 days.

(21) Appl. No.: 10/149,837

(22) PCT Filed: Apr. 27, 2000

(86) PCT No.: PCT/KR00/00400

§ 371 (c)(1),
(2), (4) Date: Jun. 14, 2002

(87) PCT Pub. No.: WO01/43690

PCT Pub. Date: Jun. 21, 2001

(30) Foreign Application Priority Data

Dec. 15, 1999 (KR) .......................... 1999-58023

(51) Int. Cl.[7] .............................................. A61B 17/00
(52) U.S. Cl. ....................................... 606/204; 606/189
(58) Field of Search .................................. 606/189, 185, 606/204

(56) References Cited

U.S. PATENT DOCUMENTS 3,992,689 A * 11/1976 Kaplow ....................... 335/302
6,113,620 A * 9/2000 Chung ........................ 606/189

FOREIGN PATENT DOCUMENTS

| KR | 84-1937 | 5/1984 |
| KR | 20-1985-000123 2 | 4/1985 |
| KR | 20-1991-000032 0 | 1/1991 |
| KR | 0133133 | 12/1997 |

* cited by examiner

Primary Examiner—David O. Reip
Assistant Examiner—D. Jacob Davis
(74) Attorney, Agent, or Firm—Dann, Dorfman, Herrell & Skillman, P.C.; Henry H. Skillman

(57) ABSTRACT

A device for acupuncture is disclosed. The device has a pressure plate 100 having a polygonal profile. Both a magnet 300 and a magnetic body 400 are set in the pressure plate 100, with the magnetic body 400 being brought into contact with the magnet 300 at its upper end. The magnetic body 400 also extends through the pressure plate 100 so as to project outside the lower surface of the plate 100 at its lower end. The pressure plate 100 is also provided with both a plurality of fitting rods 130 and the same number of channelled fitting tubes 140. When it is desired to assemble two or more pressure plates 100 into an assembly, the fitting rods 130 of one plate 100 are elastically coupled to the channelled fitting tubes 140 of another plate 100. A cap 200 is mounted to the upper surface of the plate 100 and seats both the magnet 300 and the magnetic body 400 therein. A tubular member 500 is fitted into the pressure plate 100 from the lower surface of the plate 100 and is locked to the cap 200 at its upper end. The tubular member 500 has a central bore 530 allowing the magnetic body 400 to axially extend through until the conical tip of the magnetic body 400 projects outside the lower surface of the plate 100. This device is formed as a unit cell, and so two or more devices are easily and orderly coupled to each other into an acupuncture assembly, having desired size and shape, when necessary. The device of this invention may be attached to a desired part of the body using a band or may be coupled to each other into a bed mattress-sized assembly preferably usable as a healthful mattress for beds. This device thus allows a user to save money while purchasing such a device and gives a desired acupuncture treatment effect to the user.

12 Claims, 6 Drawing Sheets

DEVICE FOR ACUPUNCTURE

BACKGROUND OF THE INVENTION

1. Field of the Invention

The present invention relates, in general, to a device for acupuncture and, more particularly, to a structural improvement in such an acupuncture device to directly apply the healthful far infrared rays, anions and lines of magnetic force onto the human body and to allow a user to easily and simply fabricate an acupuncture assembly, having desired shape and size, by appropriately assembling a plurality of acupuncture devices individually formed as a unit cell, having predetermined shape and size, into a desired assembly.

2. Description of the Related Art

As well known to those skilled in the art, a radiation of far infrared rays, anions and lines of magnetic force onto a specified area on the human body is very healthful to the human body, and so several types of devices for acupuncture designed to radiate such far infrared rays, anions and lines of magnetic force onto a desired specified area on the human body have been proposed and used.

However, conventional devices for acupuncture are problematic as follows. As shown in FIG. 1a, a magnetic body 20, provided at a position around a magnet 10, has a flat surface at its body contact portion.

Due to such a flat surface of the body contact portion of the magnetic body 20, the lines of magnetic force, emitted from the magnet 10 and passing through the magnetic body 20, fail to be concentrated onto a desired specified spot on the skin of the human body, may be undesirably dispersed, thus almost failing to accomplish a desired acupuncture treatment effect.

Another problem resides in that their radiation members for emitting far infrared rays, anions and lines of magnetic force are separately manufactured and are separately sold in markets, thus forcing users to separately purchase them while paying excessive money and to use them separately during an acupuncture treatment and thereby being very inconvenient to the users. Such separate radiation members, designed to separately emit far infrared rays, anions and lines of magnetic force, also prevent acupuncture devices to accomplish a desired synergistic effect expected from a combination use of all of such radiation members during the acupuncture treatment.

In an effort to overcome the problems experienced in such conventional devices for acupuncture, the inventor of this invention proposed devices for acupuncture in Korean Patent Nos. 133,133 and 198,982. In each of the above devices of this inventor, the magnetic body 400, provided at a position around a magnet 300 as shown in FIG. 1b, has a conical shape at its body contact portion. Therefore, these devices both somewhat effectively concentrate the lines of magnetic force from the magnet 300 at the point of the conical portion of the magnetic body 400, thus improving the concentration effect of the lines of magnetic force. This finally accomplishes a desired acupuncture treatment effect. The above devices for acupuncture of this inventor also have an integrated permanent magnet designed to commonly radiate desired far infrared rays, anions and lines of magnetic force at the same time and to radiate the highly intensive far infrared rays, anions and lines of magnetic force onto a desired part of the human body at the same time.

SUMMARY OF THE INVENTION

Accordingly, the present invention has been made keeping in mind the above problems occurring in the prior art, and an object of the present invention is to provide a device for acupuncture, which is formed as a plate-type unit cell for acupuncture, the unit cell being designed to be usable separately and independently or to be usable as an acupuncture assembly with a plurality of unit cells being coupled to each other into a plate-type assembly having desired shape and size.

Another object of the present invention is to provide a device for acupuncture, of which the plate-type unit cell is designed to be easily assembled with one or more additional unit cells into a plate-type assembly having a desired area.

A further object of the present invention is to provide a device for acupuncture, which has an integrated radiation member capable of commonly radiating desired far infrared rays, anions and lines of magnetic force at the same time, and which is structurally designed to allow desirably intensive far infrared rays, anions and lines of magnetic force from the integrated radiation member to be concentratively radiated onto a desired specified area of the human body, and thereby to maximize the desired synergistic effect.

In order to accomplish the above objects, an embodiment of the present invention provides a device for acupuncture, comprising: a pressure plate having a central opening at a center thereof; a cap mounted to the upper surface of the pressure plate and seating a permanent magnet therein; a magnetic body seated in the cap while being brought into contact with the magnet at its upper end within the cap, the magnetic body extending through the central opening of the pressure plate so as to project outside the lower surface of the pressure plate at its lower end; and a support means for holding the cap, the permanent magnet and the magnetic body on the pressure plate. The support means is a tubular member, which is fitted into the central opening of the pressure plate from the lower surface of the plate and is locked to the cap at its upper end, with the magnetic body axially extending through the tubular member. The lower end of the magnetic body has a conical shape with a sharpened tip.

In the above device, the pressure plate has a polygonal profile. The tubular member has a flange at its upper end, with a cylindrical fitting hub being defined on the external surface of the tubular member at a position under the flange. On the other hand, the cap has a central hole on its bottom wall. The flange of the tubular member is seated on and stopped by the interior surface of the edge of the central hole of the cap, thus locking the tubular member to the cap. The magnetic body is also flanged on its upper end coming into contact with the magnet, thus having a seat flange at the upper end. The above seat flange of the magnetic body is seated on the upper end of the tubular member, thus holding a position of the magnetic body relative to the tubular member.

The above tubular member is made of a plastic material mixed with an anion emitting material and/or a far infrared ray emitting material.

Meanwhile, the pressure plate is provided with a prominence and depression structure allowing two or more pressure plates to be assembled with each other into an assembly when necessary. The prominence and depression structure is composed of both a fitting rod and a channelled fitting tube, with the fitting rod of one pressure plate being elastically fitted into the channelled fitting tube of another pressure plate when two or more pressure plates are assembled into an assembly. In another embodiment, the pressure plate is provided with both hook and pile pieces of a Velcro fastener, allowing two or more pressure plates to be assembled with each other into an assembly when necessary, in place of the prominence and depression structure.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE PREFERRED EMBODIMENTS

Hereinafter, preferred embodiment of the present invention will be described in detail with reference to the accompanying drawing.

Figure 1A:
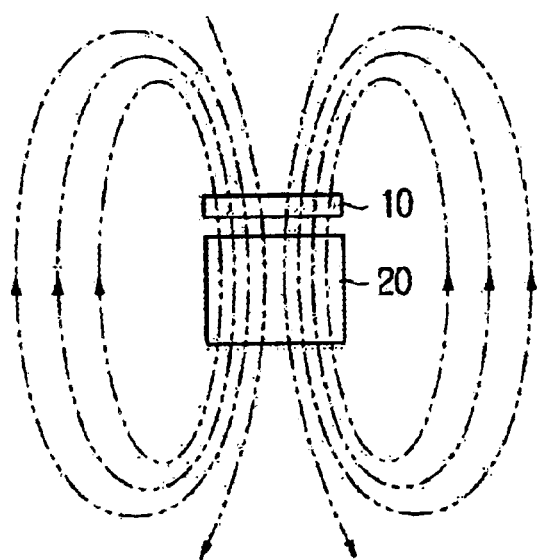
FIG. 1a is a view, showing the lines of magnetic force radiated from a flat magnetic body in a device for acupuncture in accordance with an embodiment of the prior art.
Figure 1B:
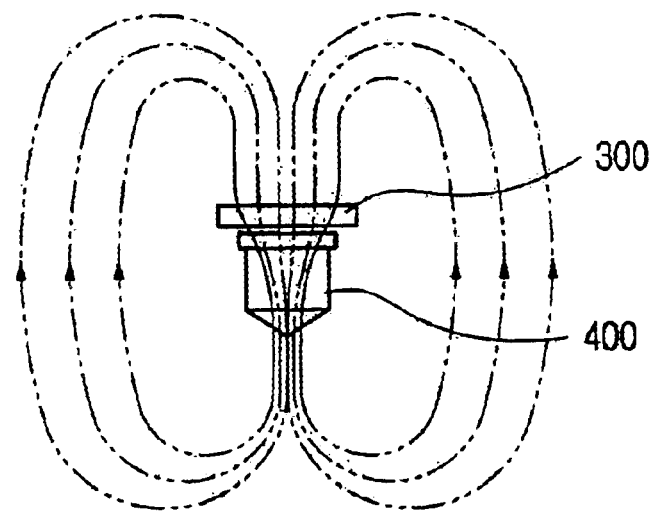
FIG. 1b is a view, showing the lines of magnetic force radiated from a conical magnetic body in a device for acupuncture in accordance with another embodiment of the prior art.
Figure 2:
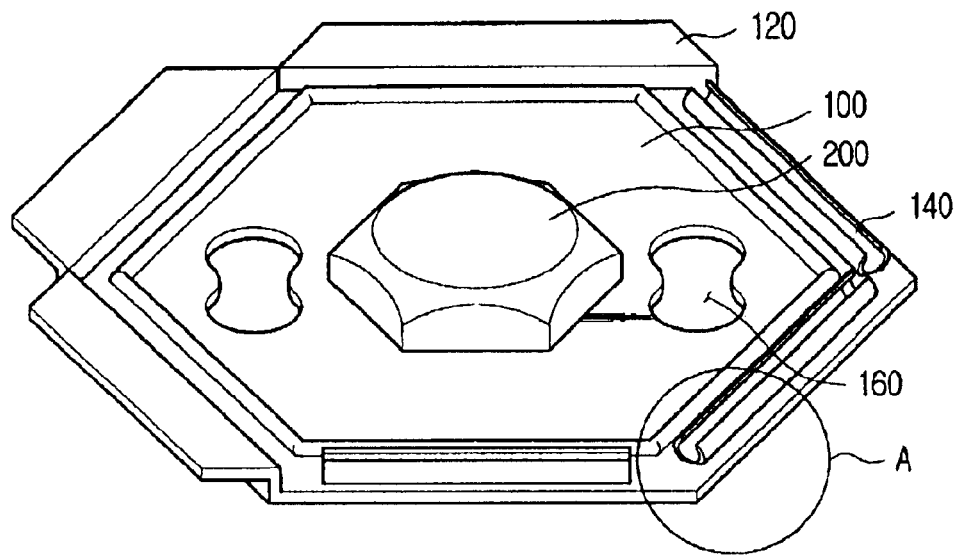
FIG. 2 is a top perspective view of an acupuncture device formed as a plate-type unit cell in accordance with the primary embodiment of the present invention.
Figure 3:
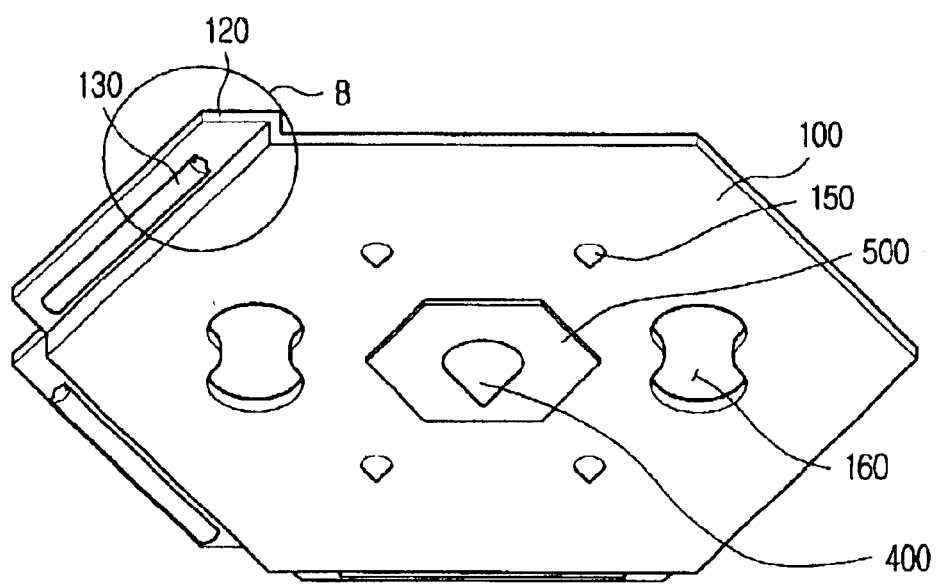
FIG. 3 is a bottom perspective view of the device of FIG. 2.
Figure 4:
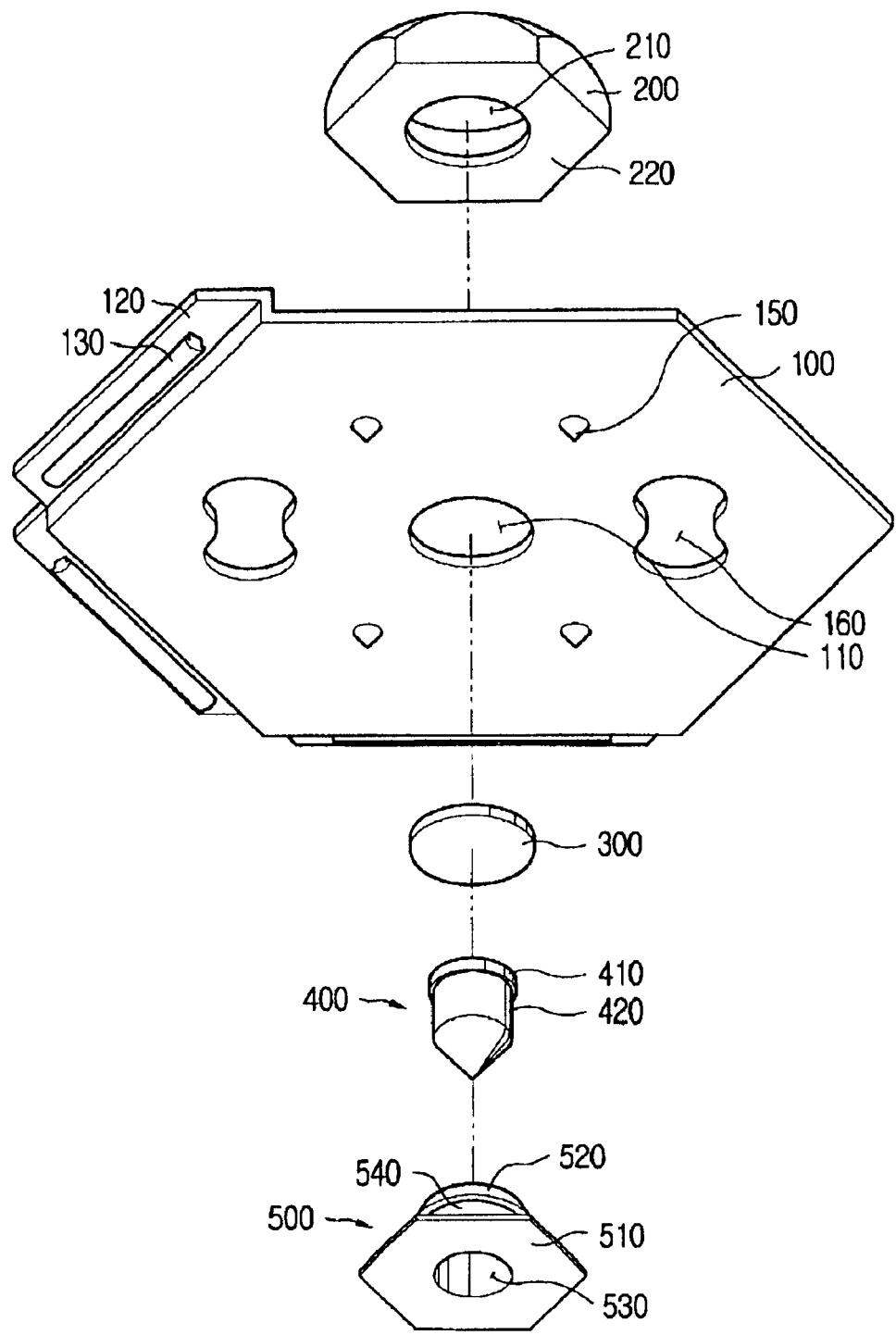
FIG. 4 is an exploded perspective view of the device of FIG. 2.

FIGS. 2 to 4 show an acupuncture device formed as a plate-type unit cell in accordance with the primary embodiment of the present invention. As shown in the drawings, the acupuncture device of this invention is formed as a plate-type unit cell for acupuncture. This unit cell is composed of a pressure plate 100, with a cap 200 having a regular hexagonal of the pressure plate 100. Both a magnet 300 and a magnetic body 400 are set within the cap 200 in a way such that the magnet 300 positioned on the interior surface of the top wall of said cap 200, with the magnetic body 400 coming into contact with the lower surface of the magnet 300 at its top surface and extending downwardly to be partially exposed outside the lower surface of the pressure plate 100 at its lower conical tip. A tubular member 500 is firmly fitted in a central opening of the pressure plate 100 and is caught by the holed bottom wall of the cap 200 at its annular top flange. The magnetic body 400 passes through the tubular member 500 while extending downwardly from the magnet 300 to the outside of the lower surface of the pressure plate 100. A cell coupling means is provided on the pressure plate 100 of the device for allowing a plurality of devices to be coupled to each other into an acupuncture assembly, having desired shape and size, when necessary.

The pressure plate 100 is a regular hexagonal plate body made of a plastic material and has an opening 110 at the center thereof, and receives the tubular member 500 at the opening 110. Four conical pressure projections 150 are regularly formed on the lower surface of the pressure plate 100 at diametrically opposite positions around the opening 110. Provided on opposite side portions of the pressure plate 100 at positions outside the central opening 110 are two air circulation holes 160. These air circulation holes 160 allow moisture, caused by, for example, perspiration, to effectively evaporate from the skin of the human body when the device is set on the skin.

In the device for acupuncture of this invention, the cell coupling means is integrally formed along the edge of the top surface of the regular hexagonal pressure plate 100.

Figure 7A:
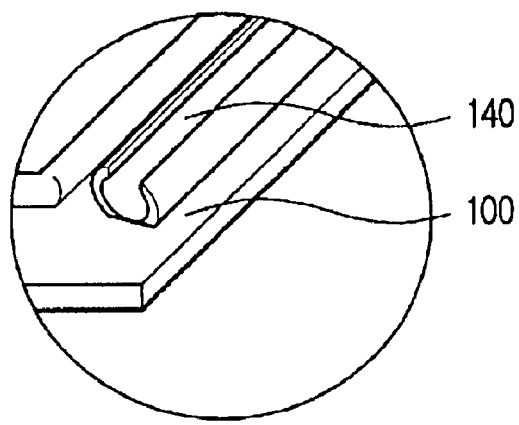
FIGS. 7a and 7b are perspective views, showing a coupling structure provided on the acupuncture device of this invention
Figure 7B:
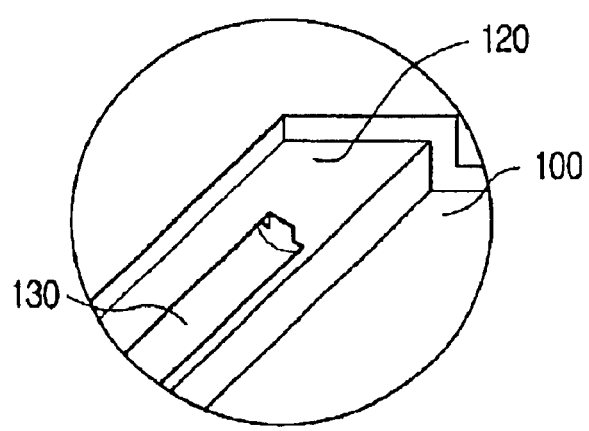

As shown in FIG. 7b, the cell coupling means comprises a prominence and depression structure composed of three bent linear flanges 120, which are formed along three continued edges of the six edges of the regular hexagonal pressure plate 100. Each of the three bent linear flanges 120 is primarily bent upwardly at right angles prior to being secondarily bent outwardly at right angles. A fitting rod 130 is integrally and longitudinally formed on the lower surface of the outwardly extending portion of each bent linear flange 120.

The cell coupling means also comprises three channelled fitting tubes 140, which are integrally and longitudinally formed on the upper surface of the remaining three edges of the regular hexagonal pressure plate 100 as best seen in FIG. 7a. Each of the three fitting tubes 140 has a longitudinal channel capable of elastically receiving an associated fitting rod 130 of a neighboring device through a snap fitting process when two or more devices are coupled into a desired assembly. In the primary embodiment, the cell coupling means comprises three fitting rods 130 and three channelled fitting tubes 140 as described above. However, it should be understood that the cell coupling means, provided on the device of this invention, may comprise the hook and pile pieces of three sets of Velcro fasteners in place of the fitting rods and channelled fitting tubes without affecting the functioning of this invention. The above tubular member 500 is designed to be firmly fitted into and set in the central opening 110 of the pressure plate 100 as shown in FIG. 4. This tubular member 500 has a cylindrical body, with a regular hexagonal base 510 formed at the lower end of that member 500 by outwardly and horizontally extending from the circular edge of said lower end. An annular top flange, having a size smaller than that of the hexagonal base 510, is formed at the upper end of the tubular member 500 by extending horizontally and outwardly. A cylindrical fitting hub 520 is thus defined between the top flange and the lower hexagonal base 510 of the tubular member 500 and is positioned within the central opening 110 of the pressure plate 100. A central bore 530 is axially and completely formed from the upper end to the lower end of the tubular member 500 and allows the magnetic body 400 to pass through.

The tubular member 500 is preferably cast into a single body using a plastic material mixed with at least one of a material capable of emitting anions and a material capable of emitting far infrared rays, such as a bioceramic material. Therefore, the tubular member 500 radiates anions and/or far infrared rays onto a desired part of the skin of the human body, thus activating the blood circulation at that part and promoting a self-production of interferon in the human body and thereby maximizing the acupuncture treatment effect.

Figure 5:
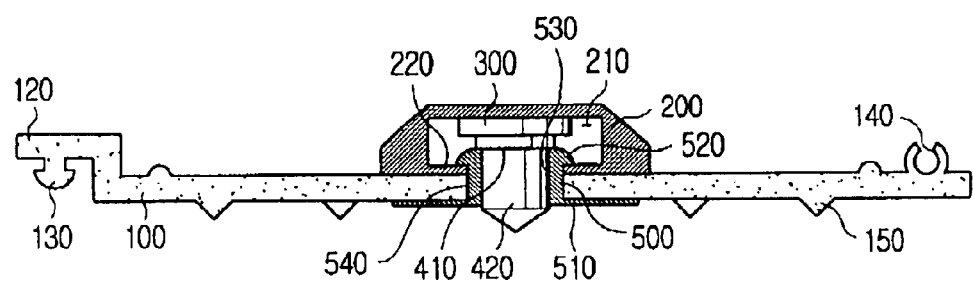
FIG. 5 is a sectional view of the device of FIG. 2.

On the other hand, the cap 200 is a regular hexagonal hollow body having an interior chamber 210 designed to seat both the magnet 300 and the magnetic body 400 therein. The magnetic body 400 is an integrated body composed of a cylindrical part and a conical tip formed at the end of the cylindrical part. The bottom wall 220 of the cap 200 is holed at the center, thus forming a central hole. The upper end portion of the fitting hub 520 of the tubular member 500 is positioned within the central hole of the cap 200, with the top flange of the tubular member 500 being firmly caught by the edge of said central hole within the chamber 210 of the cap 200. The remaining part of the fitting hub 520 of the tubular member 500 is set in the central opening 110 of the pressure plate 100. The pressure plate 100, the cap 200 and the tubular member 500 are thus somewhat closely and firmly assembled into a single body as best seen in FIG. 5.

The magnetic body 400 is made of a conductive metal and has a conical tip at its lower end, with an annular top seat flange 410 horizontally and outwardly extending from the edge of the top end of the magnetic body 400. The magnetic body 400 is brought into contact with the lower surface of the magnet 300 at its top surface. When the magnetic body 400 is received into the central bore 530 of the tubular member 500, the top seat flange 410 of the magnetic body 400 is seated on and stopped by the annular top surface of the top flange of the tubular member 500. It is thus possible for the magnetic body 400 to be stably held in the tubular member 500 without being undesirably removed from that member 500.

Figure 6:
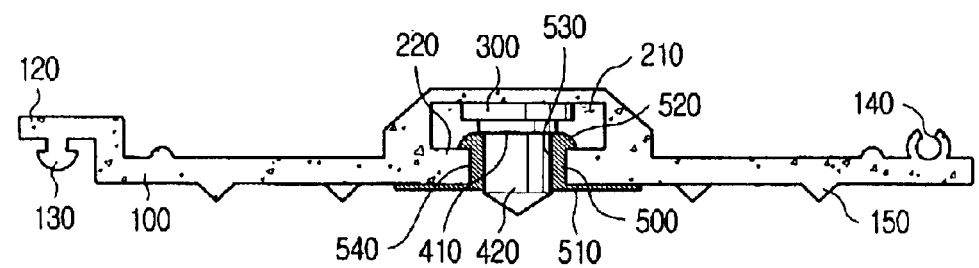
FIG. 6 is a sectional view of an acupuncture device formed as a plate-type unit cell in accordance with the second embodiment of the present invention.

In the acupuncture device according to the second embodiment of FIG. 6, the cap is cast with the pressure plate 100 into a single structure through an injection molding process different from the cap 200 of the primary embodiment, which is separately produced prior to being assembled with the pressure plate 100 into a desired unit cell. In the device of this embodiment, the construction and relative position of the magnet 300, the magnetic body 400 and the tubular member 500 remain the same as those of the primary embodiment and further explanation is thus not deemed necessary.

The device for acupuncture according to the primary embodiment of this invention will be fabricated and operated as follows.

In order to fabricate the acupuncture device according to the primary embodiment of this invention, the magnet 300 is primarily set within the chamber 210 of the cap 200 and the magnetic body 400 is secondarily set within the chamber 210. On the other hand, the tubular member 500 is fitted into the central opening 110 of the pressure plate 100. In such a case, the cylindrical fitting hub 520 of the tubular member 500 is positioned within the opening 110, with the top flange and the hexagonal base 510 of the tubular member 500 being positioned outside the upper and lower surfaces of the pressure plate 100. The tubular member 500 is thus assembled with the pressure plate 100.

Thereafter, the separately produced cap 200 is assembled with the tubular member 500 at a position on the upper surface of the pressure plate 100. When the cap 200 is precisely fitted over the fitting hub 520 of the tubular member 500 on the upper surface of the plate 100, the magnetic body 400 is inserted into the central bore 530 of the tubular member 500 until the conical tip of the magnetic body 400 is completely exposed outside the lower end of the tubular member 500 on the lower surface of the pressure plate 100. On the other hand, the top seat flange of the magnetic body 400 is seated on and stopped by the annular top surface of the tubular member 500. The magnetic body 400 is thus stably held in the tubular member 500 without being undesirably removed from that member 500. In such a case, the fitting hub 520 of the tubular member 500 is positioned within both the central hole formed on the bottom wall of the cap 200 and the central opening 110 of the pressure plate 100. The top flange of the tubular member 500 is firmly caught by the edge of the central hole of the bottom wall within the chamber 210 of the cap 200, while the hexagonal base 510 of the tubular member 500 is caught by the edge around the central opening 110 of the pressure plate 100 on the lower surface of that plate 100. The pressure plate 100, the tubular member 500 and the cap 200 having both the magnet 300 and the magnetic body 400 are thus closely and firmly assembled into a desired acupuncture device of this invention.

Figure 8:
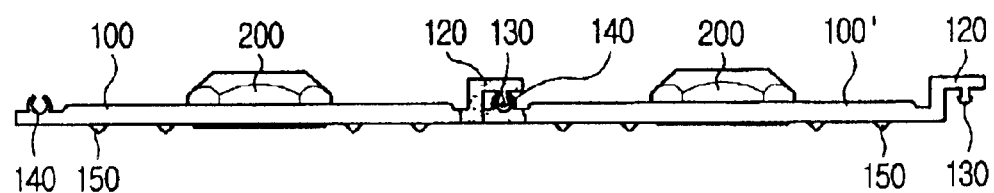
FIG. 8 is a side view of two acupuncture devices of this invention coupled to each other into a desired assembly.
Figure 9:
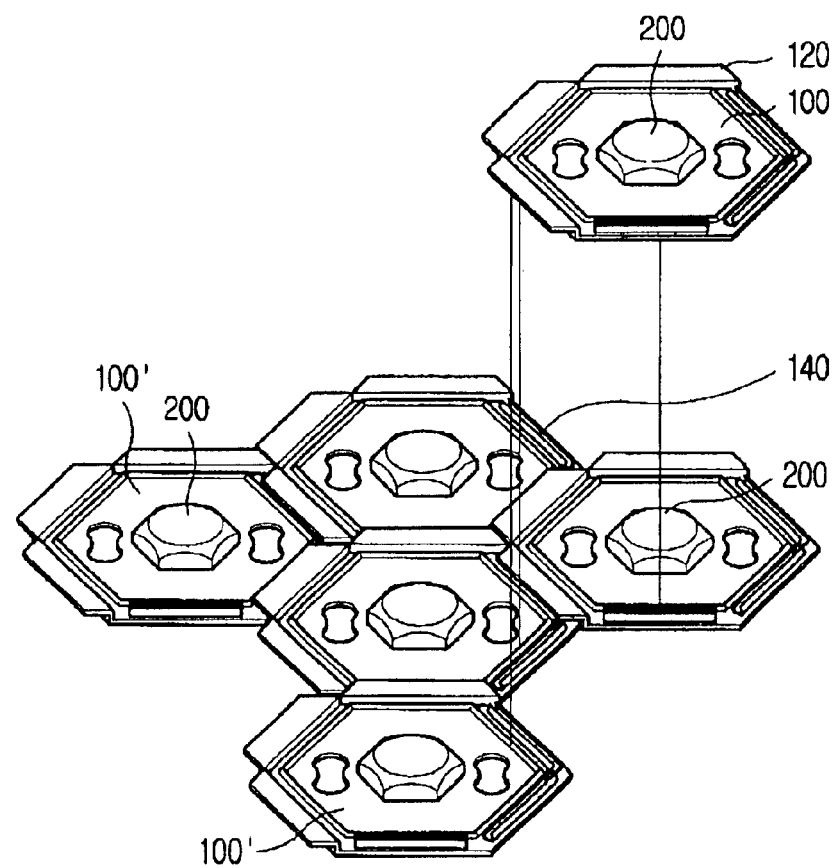
FIG. 9 is a top perspective view of a plurality of acupuncture devices of this invention coupled to each other into a desired assembly.

As shown in FIG. 8 and FIG. 9, it is possible for a user to easily fabricate an acupuncture assembly, having desired shape and size, using two or more acupuncture devices formed as unit cells. In the case of assembling two devices into an assembly, the two devices are easily integrated into a desired body by elastically locking a fitting rod 130 provided on the edge of the pressure plate 100 of one device, or a first coupling member of the first device, into a channelled fitting tube 140 of the pressure plate 100' of the other device, or a second coupling member of the second device.

When it is desired to assemble three or more devices of this invention into an assembly, the devices, formed as unit cells, are easily and orderly coupled to each other by locking the fitting rods 130 into the channelled fitting tubes 140 in the same manner as described above. It is thus possible for a user to easily and simply form an acupuncture assembly, having desired size and shape, using two or more devices.

Therefore, it is desired to form an assembly for acupuncture by coupling a desired number of devices to each other in a radial direction. That is, it is possible for a user to easily fabricate a desired acupuncture assembly using the devices of this invention regardless of the size or shape of the target assembly. In the present invention, the device for acupuncture may be produced as a larger module formed by an integration of two or three unit cells.

The acupuncture device of this invention may be produced as a very small unit cell, having a palmtop size or a very small portable size, or may be used as a unit cell of a very large assembly having a bed mattress size. The users are allowed to purchase a desired number of devices for acupuncture at the same time or separately. The device for acupuncture of this invention thus effectively accomplishes a desired acupuncture treatment effect expected by a radiation of far infrared rays, anions and lines of magnetic force onto a desired part of the human body. As described above, the present invention provides a device for acupuncture. This device is formed as a plate-type unit cell for acupuncture, the unit cell being designed to be usable separately and independently or to be usable as an acupuncture assembly with a plurality of unit cells being coupled to each other into a plate-type assembly, having desired shape and size meeting the shape and size of a selected part of the human body to be cured by the assembly. The device for acupuncture of this invention may be attached to a desired part of the human body using a band during an acupuncture treatment process. A plurality of devices may be coupled to each other into a desired assembly having a bed mattress size. The device for acupuncture of this invention thus allows a user to save money while purchasing such a device and gives a desired acupuncture treatment effect to the user.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A device for acupuncture, comprising:
   a pressure plate having a central opening at a center thereof;
   a cap mounted to a upper surface of said pressure plate and seating a permanent magnet therein,
   a magnetic body seated in said cap while being brought into contact with said magnet at a upper end thereof within the cap, said magnetic body extending through the central opening of the pressure plate so as to project outside a lower surface of said pressure plate at a lower end thereof and concentrating the lines of the magnetic force emitted from said permanent magnet thereby; and
   support means for holding said cap, said permanent magnet and said magnetic body on the pressure plate.

2. The device according to claim 1, wherein said support means is a tubular member, said tubular member being fitted into said central opening of the pressure plate from the lower surface of said plate and being locked to said cap at its first end, with said magnetic body axially extending through said tubular member.

3. The device according to claim 2, wherein said tubular member has a flange at its upper end, with a fitting hub being defined on an external surface of the tubular member at a position under said flange, and said cap has a central hole on its bottom wall, whereby the flange of the tubular member is seated on and stopped by an interior surface of an edge of said central hole of the cap, thus locking the tubular member to the cap.

4. The device according to claim 2, wherein said magnetic body is flanged on its first end coming into contact with the magnet, thus having a seat flange at said upper end, said seat flange of the magnetic body being seated on the first end of said tubular member, thus holding a position of said magnetic body relative to the tubular member.

5. The device according to claim 1, wherein said pressure plate has a polygonal profile.

6. The device according to claim 1, wherein said pressure plate is provided with a prominence and depression structure allowing two or more pressure plates to be assembled with each other into an assembly when necessary.

7. The device according to claim 6, wherein said prominence and depression structure is composed of both a fitting rod and a channelled fitting tube, with the fitting rod of one pressure plate being elastically fitted into the channelled fitting tube of another pressure plate when two or more pressure plates are assembled into an assembly.

8. The device according to claim 1, wherein said pressure plate is provided with both hook and pile pieces of a Velcro fastener allowing two or more pressure plates to be assembled with each other into an assembly when necessary.

9. The device according to claim 1, wherein the lower end of said magnetic body has a conical shape with a sharpened tip.

10. A device for acupuncture, comprising:
    a pressure plate having a permanent magnet in a chamber formed on a upper surface of the plate;
    a magnetic body set in said pressure plate while being brought into contact with said magnet at a upper end thereof and projecting outside a lower surface of said pressure plate at a lower end thereof; and
    a tubular member fitted into said pressure plate and holding both said permanent magnet and said magnetic body on the pressure plate, said tubular member having a central bore allowing said magnetic body to axially extend through until the magnetic body projects outside the second lower surface of the pressure plate at its lower end.

11. The device according to claim 10, wherein said pressure plate is provided with a prominence and depression structure allowing two or more pressure plates to be assembled with each other into an assembly when necessary.

12. The device according to claim 10, wherein the lower end of said magnetic body has a conical shape.

\* \* \* \* \*